United States Patent
Tan et al.

(10) Patent No.: US 11,622,947 B2
(45) Date of Patent: Apr. 11, 2023

(54) COMPOSITIONS COMPRISING QUILLAJA EXTRACT AND METHODS OF PREPARATIONS AND USE THEREOF

(71) Applicant: American River Nutrition, LLC, Hadley, MA (US)

(72) Inventors: Barrie Tan, Hadley, MA (US); Peter James Law, Hadley, MA (US); Weipeng Qi, Hadley, MA (US)

(73) Assignee: American River Nutrition, LLC, Hadley, MA (US)

(*) Notice: Subject to any disclaimer, the term of this patent is extended or adjusted under 35 U.S.C. 154(b) by 308 days.

(21) Appl. No.: 16/888,183

(22) Filed: May 29, 2020

(65) Prior Publication Data

US 2020/0375920 A1    Dec. 3, 2020

Related U.S. Application Data

(60) Provisional application No. 62/855,861, filed on May 31, 2019.

(51) Int. Cl.
| | |
|---|---|
| *C07C 1/00* | (2006.01) |
| *A61K 31/122* | (2006.01) |
| *A61K 36/185* | (2006.01) |
| *A61K 47/24* | (2006.01) |
| *A61K 47/14* | (2017.01) |
| *A23L 33/115* | (2016.01) |
| *A23P 10/22* | (2016.01) |
| *A23P 10/40* | (2016.01) |
| *A23L 3/46* | (2006.01) |
| *A23L 33/105* | (2016.01) |

(52) U.S. Cl.
CPC .............. *A61K 31/122* (2013.01); *A23L 3/46* (2013.01); *A23L 33/105* (2016.08); *A23L 33/115* (2016.08); *A23P 10/22* (2016.08); *A23P 10/40* (2016.08); *A61K 36/185* (2013.01); *A61K 47/14* (2013.01); *A61K 47/24* (2013.01); *A23V 2002/00* (2013.01)

(58) Field of Classification Search
CPC ......................................................... C07D 1/00
See application file for complete search history.

(56) References Cited

U.S. PATENT DOCUMENTS

| | | |
|---|---|---|
| 2005/0184275 A1 | 8/2005 | Mora-Gutierrez et al. |
| 2005/0208083 A1 | 9/2005 | Annis |
| 2008/0274195 A1 | 11/2008 | Nicolosi et al. |
| 2009/0018186 A1 | 1/2009 | Chen et al. |
| 2010/0151061 A1 | 6/2010 | Morariu |
| 2011/0206739 A1 | 8/2011 | Nicolosi et al. |
| 2011/0236364 A1 | 9/2011 | Bromley |

(Continued)

FOREIGN PATENT DOCUMENTS

WO    2013135759 A1    9/2013

OTHER PUBLICATIONS

Minekus et al., Food & Function, 5 (6) (2014), pp. 1113-1124.
(Continued)

*Primary Examiner* — Rosanne Kosson
(74) *Attorney, Agent, or Firm* — Troutman Pepper Hamilton Sanders LLP

(57) ABSTRACT

The present embodiments are directed to compositions comprising *quillaja* extract and at least one active ingredient such as nutritional supplement, dietary ingredient, medicine, and food additive, and methods for preparations and use thereof.

17 Claims, 7 Drawing Sheets
(6 of 7 Drawing Sheet(s) Filed in Color)

(56) References Cited

U.S. PATENT DOCUMENTS

2013/0029884 A1   1/2013   Malchesky et al.
2013/0189316 A1   7/2013   Chen
2013/0309362 A1   11/2013  Bromley
2015/0030748 A1   1/2015   Schultz et al.

OTHER PUBLICATIONS

Chait, et al., LWT—Food Science and Technology 117 (2020) 1086233.
Saudek et al., N. Engl. J. Med., 1989, 321, 574.
Levy et al., Science, 1985, 228, 190.
During et al., Ann. Neurol., 1989, 25, 351.
Howard et al., J. Neurosurg., 1989, 71, 105.
Langer, Science, 1990, 249, 1527-1533.
Rajewski et al., Journal of Pharmaceutical Sciences, 1996, 85, 1155-1159.
Mei Hang Ng et al, Separation of vitamin E (tocopherol, tocotrienol and tocomonoenol) in Palm oil; Lipids, vol. 39, No. 10 (2004).
SIGMA, Saponin from Quillaja Bark, Product Information, Obtained online on Aug. 22, 2016.
Non-Final Office Action dated Aug. 25, 2016 in U.S. Appl. No. 14/866,726.
Final Office Action dated Mar. 3, 2017 in U.S. Appl. No. 14/866,726.
Non-Final Office Action dated Aug. 21, 2017 in U.S. Appl. No. 14/866,726.
Final Office Action dated Apr. 5, 2018 in U.S. Appl. No. 14/866,726.

10 min 30 min 2 hr 4 hr 10 min 30 min 2 hr 4 hr 10 min 30 min 2 hr 4 hr 10 min 30 min 2 hr 4 hr 10 min 30 min 2 hr 4 hr 10 min 30 min 2 hr 4 hr Sample A contains ubiquinol*, MCT, sunflower lecithin.
Sample B contains ubiquinol*, MCT, sunflower lecithin, and quillaja extract

* Prepared according to U.S. Patent Application No.16/829,868

|  | Sample A (by Weight) | Sample B (by Weight) |
| --- | --- | --- |
| Ubiquinol* | 25% | 25% |
| Medium-Chain Triglyceride (MCT) | 50% | 50% |
| Lecithin | 25% | 21% |
| Quillaja Powder | 0% | 4% |

COMPOSITIONS COMPRISING QUILLAJA EXTRACT AND METHODS OF PREPARATIONS AND USE THEREOF

CROSS-REFERENCE TO RELATED APPLICATIONS

This application claims priority to U.S. Provisional Application No. 62/855,861, filed May 31, 2019, which is incorporated herein by reference in its entirety.

FIELD

Embodiments disclosed herein are directed to compositions of *quillaja* extract and at least one active ingredient, such as nutritional supplements, dietary ingredients, medicines, and food additives, and methods for preparations and use thereof.

BACKGROUND

Lipid soluble active ingredients such as nutritional supplements, dietary ingredients, medicines, and food additives generally lack bioavailability due to their poor solubilities. To improve bioavailabilities of such ingredients, excipients have been utilized to facilitate dissolution, dispersion, and/or self-emulsification of active ingredients. For example, self-emulsifying formulations of the ingredients are readily dispersed in the GI tract, which increases the bioaccessiblity of them for absorption and, as a result, increases the bioavailability thereof. The use of natural excipients is preferred by the public due to their advantages such as being a renewable resource (e.g., non-exhaustible), ecological (i.e. more biodegradable with environmental and aquatic safety), safe (e.g., hypo-allergenic, non-toxic).

Although various excipients have been used to increase the bioavailability of ingredients, there is still a need for new ones that can perform better and increase bioavailability.

Thus, there is a need for such compounds and compositions. The embodiments provided for herein satisfies these needs as well as others.

SUMMARY OF EMBODIMENTS

In some embodiments, compositions of *quillaja* extract and at least one active ingredient are provided. Active ingredients include, but limited to nutritional supplement, dietary ingredient, medicine, and food additive. In some embodiments, methods for preparing the compositions are provided as described herein. In some embodiments, methods of increasing the bioaccessibilities and bioavailabilities of the active ingredients described herein are provided. In some embodiments, methods of increasing the bioaccessibilities and bioavailabilities of CoQ10, quercetin, and berberine with *quillaja* extract are provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Figure 1:
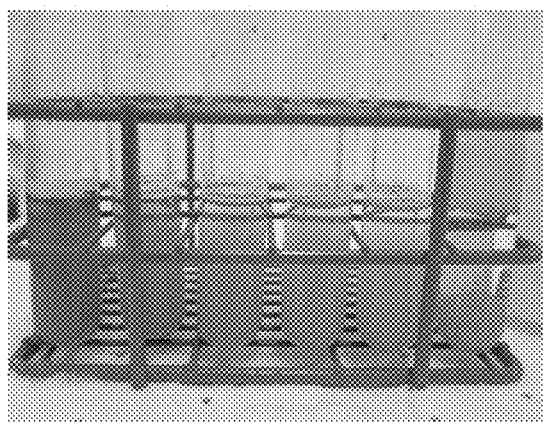
FIG. 1 illustrates dispersibilities of certain compositions comprising CoQ10 powder and *quillaja* extract in certain ratios.
Figure 1:
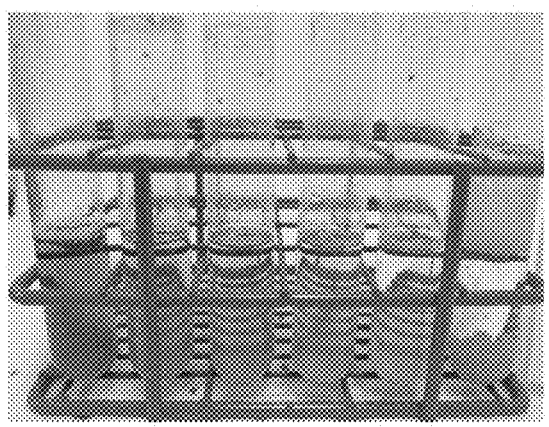
Figure 1:
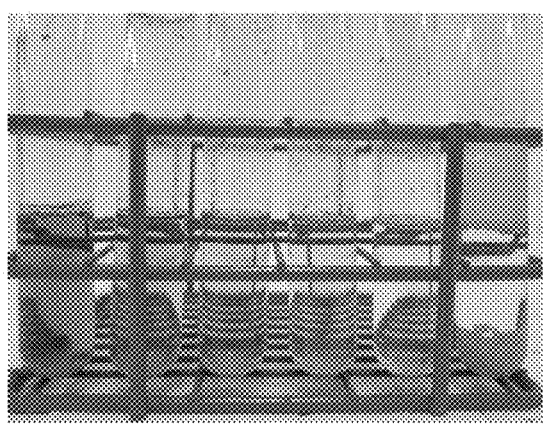
Figure 1:
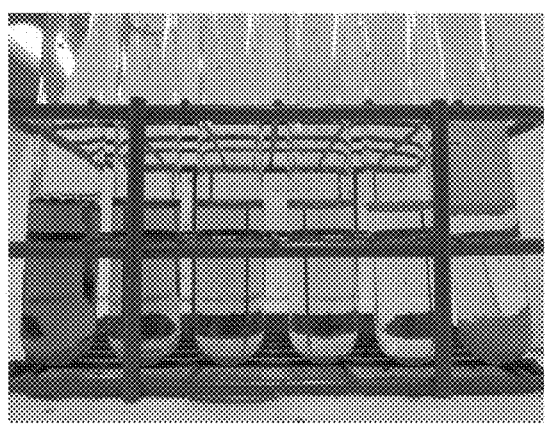

Unless defined otherwise, all technical and scientific terms have the same meaning as is commonly understood by one of ordinary skill in the art to which the embodiments disclosed belongs.

As used herein, the terms "a" or "an" mean that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Embodiments provided for herein demonstrate the use of *quillaja* powder (*quillaja* extract) can be combined with other ingredients or compounds to increase the bioavailability of the other ingredients or compounds. Therefore, in some embodiments, compositions comprising *quillaja* extract and at least one other ingredient are provided, wherein the bioavailability of the at least one other ingredient is increased as compared to a composition without the *quillaja* extract.

As used herein, the term "an active ingredient" or "an active powder" refers to a nutritional supplement, a medicine, or food additive, which is a lipid powder or a liquid oil that can be made into a powder that is supposed to have a therapeutic effect or is an ingredient or composition taken orally that contains one or more ingredients (such as those provided for herein) that are intended to supplement a subject's diet and are not considered food. A nutritional supplement can also be referred to as a dietary supplement. A dietary supplement refers to a product or composition, but not including tobacco, which is intended to supplement the diet of a subject that bears or contains one or more of the following dietary ingredients: (A) a vitamin; (B) a mineral; (C) an herb or other botanical; (D) an amino acid; (E) a dietary substance for use by man to supplement the diet by increasing the total dietary intake; or (F) a concentrate, metabolite, constituent, extract, or combination of any ingredient described in clause (A), (B), (C), (D), or (E). (see, 21 U.S.C 321 (ff)(1)). A dietary supplement can contain one or more dietary ingredients. In some embodiments, the dietary ingredient is CoQ10 or other ingredients provided for herein. Non-limiting examples of dietary ingredients, include but are not limited to: quinones (CoQ10 (reduced (ubiquinol), oxidized (ubiquinone), or a combination thereof)), menaquinones (MKs), pyrroloquinoline quinone (PQQ), cannabinoids (CBD, tetrahydrocannabinol (THC)), *curcuma* isolates (tumerones, curcumenes, xanthorrhizol, curcumin), berberine, diindolylmethane (DIM), phenolics (resveratrol, quercetin), lipid-soluble vitamins (A, D, E, K), symmetrical carotenoids (beta-carotene, zeaxanthin, lycopene, astaxanthin), omega-3's, or terpenoids (mono-terpenoids, di-terpenoids, tri-terpenoids, sesqui-terpenoids). These dietary ingredients can be used alone or in combination with the dietary ingredients provided herein or others commonly used. In some embodiments, a composition provided for herein excludes one or more of these dietary ingredients. For example, in some embodiments, a composition provided for herein does not include quinones (CoQ10 (reduced (ubiquinol), oxidized (ubiquinone), or a combination thereof)), menaquinones (MKs), pyrroloquinoline quinone (PQQ), cannabinoids (CBD, tetrahydrocannabinol (THC)), *curcuma* isolates (tumerones, curcumenes, xanthorrhizol, curcumin), berberine, diindolylmethane (DIM), phenolics (resveratrol, quercetin), lipid-soluble vitamins (A, D, E, K), symmetrical carotenoids (beta-carotene, zeaxanthin, lycopene, astaxanthin), omega-3's, or terpenoids (mono-terpenoids, di-terpenoids, tri-terpenoids, sesqui-terpenoids).

As used herein, the term "animal" includes, but is not limited to, humans and non-human vertebrates such as wild, domestic, and farm animals.

As used herein, the term "bioaccessiblity" means the fraction of the total amount of a substance (e.g. active ingredient) that is potentially available for absorption. For example in nutrition and food, bioaccessiblity refers to the quantity of a compound or an active ingredient that is released from its matrix (form in which it is ingested) in the gastrointestinal tract, becoming available for absorption (e.g. enters the blood stream).

As used herein, the term "bioavailability" means the proportion of an active ingredient, which enters the circulation when introduced into the body and so is able to have an active effect. In pharmacology, bioavailability refers to the fraction of an administered dose of the active ingredient that reaches the systemic circulation.

As used herein, the term "CoQ10" unless otherwise specified means a generic reference to ubiquinone and/or ubiquinol and to their inseparable redox system. In some embodiments, CoQ10 is reduced. In some embodiments, CoQ10 is ubiquinone.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "DI water" means deionized water.

As used herein, the term "excipients" means substances formulated alongside the active ingredient of nutritional supplements, medicaments, and/or food additives, for the purpose to confer a therapeutic enhancement on the active ingredient in the final dosage form, such as facilitating drug absorption, reducing viscosity, or enhancing solubility. In some embodiments, "excipients" means surfactants as described herein. In some embodiments, "excipients" means emulsifiers as described herein. For examples, excipients can be botanical water-soluble emulsifiers and saponins such as *quillaja* saponins, *yucca* saponins, and lecithins; gums such as guar gum, xanthan gum, cellulose gum, alginate, carrageenan, konjac gum, locust bean gum, and acacia gum; glycerides such as monoglycerides (MG), diglycerides (DG), triglycerides (TG); and other carriers including maltodextrins.

As used herein, the term "emulsifiers," which can also be referred to as "emulgents" means substances that stabilizes an emulsion by, for example, increasing its kinetic stability. In some embodiments, an "emulsifier" is a surfactant.

As used herein, the term "glycerides" means molecules derived from fatty acids, such as, but not limited to, monoglycerides (MG), diglycerides (DG), triglycerides (TG), phospholipids, lecithins, and compounds with one or more fatty acid adduct(s). In some embodiments, glycerides (mono-, di-, and tri-glycerides) are monoglycerides (MG), diglycerides (DG), triglycerides (TG), or any combination thereof.

As used herein, the terms "individual," "subject," and "patient," used interchangeably, mean any animal or pet including mammals, such as mice, rats, other rodents, rabbits, dogs, cats, swine, cattle, sheep, horses, or primates, such as humans.

As used herein, the term "lipid soluble" in reference to a compound, such as an active ingredient", is a compound that is not generally water soluble without the addition of another component added to the water.

As used herein, the term "in need thereof" in reference to a subject has been identified as having a need for the particular composition, compound, method, or treatment. In some embodiments, the subject can be in need thereof.

As used herein, the term "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

As used herein, the term "pharmaceutically acceptable" means those compounds, active ingredients (e.g., dietary ingredients), materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the term "menaquinones" or "MKs", also known as vitamin K-2, refers to a compound from the set of MK2 to MK13 quinone products, all of which are part of vitamin $K_2$, either individually or a combination of any of the same.

As used herein, the term "PQQ" means pyrroloquinoline quinone (PQQ), which can also be referred to as methoxatin.

As used herein, the term "*quillaja* powder" or "*quillaja* extract" refers to a *quillaja* extract, which can be a powder or dissolved in a solvent to be a liquid, from *quillaja saponaria*. In some embodiments, the *quillaja* extract comprises saponins, such as *quillaja* saponins. The source of the *quillaja* extract or *quillaja* powder is not critical and any source of the *quillaja* extract or *quillaja* powder can be used. The *quillaja* extract can be in a liquid or solid form. A non-limiting example of a *quillaja* powder that can be used is Foamation® Q dry Foaming Agent (Ingredion Incorporated, United States of America, 17955912) in a powder form. In some embodiments, the *quillaja* extract or *quillaja* powder comprises about 10% to about 50% by weight of saponins based on the dry-matter content. In some embodiments, the *quillaja* extract or *quillaja* powder comprises about 10% to about 40% by weight of saponins based on the dry-matter content. In some embodiments, the *quillaja* extract or *quillaja* powder comprises about 10% to about 30% by weight of saponins based on the dry-matter content. In some embodiments, the *quillaja* extract or *quillaja* powder comprises about 20% to about 30% by weight of saponins based on the dry-matter content. In some embodiments, the *quillaja* extract or *quillaja* powder comprises about 20% to about 26% by weight of saponins based on the dry-matter content.

As used herein, the term "saponins" refers to a class of chemical compounds structurally having one or more hydrophilic glycone moieties combined with a lipophilic triterpene or steroid derivative, which are found in particular abundance in various plant species. For example, *Yucca schidigera* (Mexico) and *Quillaja saponaria* (Chile) are both desert plants used as commercial sources for saponins. *Quillaja* saponins are derived from *Quillaja saponaria* and *yucca* saponins are derived from *Yucca schidigera*. The chemical structure of *quillaja* saponins consists of a hydrophilic oligosaccharide moiety glycosidically linked to a triterpenoid hydrophobic aglycone while the chemical structure of *yucca* saponins consists of a hydrophilic oligosaccharide moiety glycosidically linked to a steroid structure.

As used herein, the term "solubilizing agent" means agents that result in formation of a micellar solution or a true solution of the active ingredient. In some embodiments, the solubilizing agent is the *quillaja* extract or *quillaja* powder.

As used herein, the term "solution/suspension" means a liquid composition wherein a first portion of the active ingredient is present in solution and a second portion of the active ingredient is present in particulate form, in suspension in a liquid matrix.

As used herein, the term "surfactants" means compounds that lower the surface tension (or interfacial tension) between two liquids, between a gas and a liquid, or between a liquid and a solid. Surfactants may act as detergents, wetting agents, emulsifiers, foaming agents, and dispersants.

It is further appreciated that certain features described herein, which are, for clarity, described in the context of separate embodiments, can also be provided in combination in a single embodiment. Conversely, various features, which are, for brevity, described in the context of a single embodiment, can also be provided separately or in any suitable subcombination.

Provided herein are compositions comprising *quillaja* powder or *quillaja* extract and at least one active ingredient such as, but not limited to, a nutritional supplement, one or more dietary ingredients, a medicine, or a food additive, and methods for preparations and use thereof. Also provided herein are methods of testing the dispersibilities of the compositions described. Also provided herein are methods of increasing the bioaccessibilities and bioavailabilities of active ingredients, such as ingredients, which include those provided herein, and, for example, CoQ10 (reduced or oxidized), quercetin, or berberine with *quillaja* extract.

Accordingly, in some embodiments a composition comprising *quillaja* extract and at least one active ingredient are provided. In some embodiments, the active ingredient is as provided for herein. In some embodiments, the active ingredient is lipid soluble. In some embodiments, the active ingredient is a nutritional supplement, a dietary ingredient, a medicine, or a food additive. As provided for herein, in some embodiments, the nutritional supplement or dietary ingredient can be a quinone a pyrroloquinoline quinone (PQQ), a cannabinoid, a *curcuma* isolate, berberine, diindolylmethane (DIM), a phenolic, a lipid-soluble vitamin, a symmetrical carotenoids, an omega-3 fatty acid, or a terpenoid, or any combination thereof. In some embodiments, the nutritional supplement or dietary ingredient is CoQ10, reduced CoQ10, oxidized CoQ10, vitamin K-2, cannabidiol, tetrahydrocannabinol, tumerone, curcumene, xanthorrhizol, curcumin, berberine, diindolylmethane (DIM), resveratrol, quercetin, Vitamin A, Vitamin D, Vitamin E, Vitamin K, beta-carotene, zeaxanthin, lycopene, astaxanthin, omega-3 fatty acid, a mono-terpenoids, a di-terpenoids, a tri-terpenoids, or a sesqui-terpenoids, or any combination thereof. The dietary ingredient can also be as described elsewhere herein. In some embodiments, the dietary ingredient is CoQ10, reduced CoQ10, oxidized CoQ10, menaquinone, curcumin, berberine, diindolylmethane (DIM), resveratrol, or quercetin, or any combination thereof. In some embodiments, the at least one active ingredient is CoQ10. In some embodiments, the CoQ10 is ubiquinol, ubiquinone, or a mixture of ubiquinol and ubiquinone. In some embodiments, composition comprises a CoQ10 mixture, wherein the CoQ10 mixture is a mixture of ubiquinol and ubiquinone and wherein the ubiquinol is less than 95% by weight in the mixture as compared to the total of CoQ10. In some embodiments, the ratio of reduced CoQ10 relative to the whole amount of CoQ10 (namely the sum of reduced CoQ10 and oxidized CoQ10) is not particularly restricted but, in some embodiments, it is, for example not lower than 20% by weight of the total of CoQ10, not lower than 40% by weight of the total of CoQ10, not lower than 60% by weight of the total of CoQ10, not lower than 80% by weight of the total of CoQ10, not lower than 90% by weight of the total of CoQ10, or not lower than 95% by weight of the total of CoQ10. The upper limit is 100% by weight of the total of CoQ10 and although there are no particular limitations, it is can be, in some embodiments, 99.9% by weight of the total of CoQ10 or less.

The weight ratio of the *quillaja* extract to the at least one active ingredient can be any ratio. In some embodiments, the ratio of *quillaja* extract to the at least one active ingredient is from about 12:75 to about 75:25. In some embodiments, the weight ratio of the *quillaja* extract to the at least one active ingredient is about 12:75, about 25:75, about 40:60, about 50:50, about 67:33, or about 75:25. The ratio can be based on the weight of the *quillaja* extract to one active ingredient present in the composition or if there are more than one active ingredients, the ratio can be the ratio of the *quillaja* extract to the total weight of the active ingredients if there is more than one.

As described herein, the composition can also be provided in forms that are suitable for ingestion by a subject. In some embodiments, the composition in the form of a soft capsule, hard capsule, tablet, gel capsule, gel, softgel, 2-piece liquid-filled capsule, bar, confectionary, chocolate, powder, oral suspension, pill, hard-shell, truffle, ganache, truffle ganache, gum, or chewable form. In some embodiments, composition is a gel capsule, soft capsule, a hard capsule, or a tablet.

In some embodiments, the *quillaja* extract contains about 20% to about 30% of *quillaja* saponin by weight. In some embodiments, the *quillaja* extract comprises about 10% to about 50% by weight of saponins based on the dry-matter content. In some embodiments, the *quillaja* extract or *quillaja* powder comprises about 10% to about 40% by weight of saponins based on the dry-matter content. In some embodiments, the *quillaja* extract or *quillaja* powder comprises about 10% to about 30% by weight of saponins based on the dry-matter content. In some embodiments, the *quillaja* extract or *quillaja* powder comprises about 20% to about 30% by weight of saponins based on the dry-matter content. In some embodiments, the *quillaja* extract or *quillaja* powder comprises about 20% to about 26% by weight of saponins based on the dry-matter content.

In some embodiments, the composition comprises at least one triglyceride, at least one phospholipid, or a combination thereof. Examples of triglycerides include, but are not limited to, a medium-chain triglyceride (MCT). Examples of phospholipids include, but are not limited to, a lecithin.

In some embodiments, methods of increasing the bioaccessibility and/or bioavailability of an active ingredient in a subject are provided. The active ingredient can be any active ingredients, such as, but not limited to, those described herein. In some embodiments, the methods comprise administering to the subject any of the compositions provided for herein. The administration can be by any method, such as those described herein. For example, in some embodiments, the compositions are administered by parenteral, subcutaneous, intravenous, intramuscular, intraperitoneal, transdermal, oral, buccal, sublingual, ocular, or intravaginal administration, by inhalation, by depot injections, or by implants. In some embodiments, the administration is by oral administration. In some embodiments, the administration is by ocular administration. In some embodiments, the bioaccessibility of the at least one active ingredient is increased by about, or at least, 10%, 20%, 30%, 40%, 50%, 60%, 70%, 80%, 90%, 100%, 150%, or 200%. In some embodiments, bioaccessibility of the at least one active ingredient is increased by about 10% to about 300%, about 10% to about 200%, about 50% to about 200%, about 100% to about 200%, about 150% to about 200%, about 50% to about 150%, or about 175% to about 200%. An increase in bioaccessibility can be determined by any suitable method. For example, bioaccessibility can be measured by simulated in vitro digestion. Simulated in vitro digestion is a standard and routine model for determining bioaccessibility. One example can be found in Minekus et al., Food & Function, 5 (6) (2014), pp. 1113-1124, which is hereby incorporated by reference in its entirety. Another example can be found in Chait, et al., LWT-Food Science and Technology 117 (2020) 1086233, which is hereby incorporated by reference in its entirety. Without being bound to any particular method, in some embodiments, bioaccessibility is determined by mixing a sample (a composition) with a saliva solution and, optionally, mucin. The mixture can then be incubated with Fasted State Simulated Gastric Fluid and pepsin. The mixture can then be incubated under suitable conditions and mixed subsequently with Fasted State Simulated Intestinal Fluid (FASSIF), a bile extract solution, and a lipase solution. The samples can then be analyzed by HPLC to determine the increase in bioaccessibility. Bioaccessibility can be calculated by dividing the amount of the at least one active ingredient measured by, for example HPLC, by the theoretical (or actual amount of ubiquinol in the sample)×100 to determine the percent bioaccessibility. One non-limiting example of this is illustrated in Example F1.

In some embodiments, the subject is a subject in need thereof.

In some embodiments, method of preparing the composition described herein are provided. In some embodiments, the methods comprise mixing *quillaja* extract with the at least one active ingredient. In some embodiments, the methods further comprise incorporating, injection, or forming the composition (e.g., the mixture) into a gel capsule.

In some embodiments, methods of preparing a powder comprising *quillaja* extract and at least one active ingredient are provided. In some embodiments, the methods comprising drying a solution comprising *quillaja* extract and at least one active ingredient to form a dried solid and grinding the solid to form a powder comprising *quillaja* extract and the at least one active ingredient. In some embodiments, the drying is performed by spray drying or by stirring until the solution is dried. In some embodiments, the dried solid is a fully dried solid. In some embodiments, a fully dried solid has less than 10%, 9%, 8%, 7%, 6%, 5%, 4%, 3%, 2%, 1%, 0.5%, 0.1%, 0.01% water or liquid solvent content.

In some embodiments, the methods of preparing the powder comprises making a solution comprising *quillaja* extract and at least one active ingredient by mixing a *quillaja* extract solution with at least one active ingredient. In some embodiments, the at least one active ingredient mixed with the *quillaja* extract solution is a solid. In some embodiments, the at least one active ingredient solid is a powder. In some embodiments, the powder is a fine powder. In some embodiments, the powder has size from about 90 to about 180 microns. In some embodiments, the powder is a very fine powder, which can have a size from about 90 to about 125 microns. The size is based on the average size distribution of the powder, which can be measured using any suitable methods. In some embodiments, the powder is a fine powder, which can have a size from about 125 to about 180 microns. In some embodiments, the powder does not include particles that are larger than 180 microns in diameter. The size of the particles can be based on the $X_{50}$, which is the median particle dimension (i.e., 50% of the particles are smaller and 50% of the particles are larger). In some embodiments, the size of the particles can be based on the $X_{90}$ which is the particle dimension corresponding to 90% of the cumulative undersize distribution.

In some embodiments, the method further comprises grinding the at least one active ingredient to form the powder.

In some embodiments, the method comprises preparing the *quillaja* extract solution. In some embodiments, preparing the *quillaja* extract solution comprises mixing *quillaja* extract in water to form the *quillaja* extract solution.

In some embodiments, the method comprises preparing a gel capsule comprising the powder comprising *quillaja* extract and the at least one active ingredient.

In some embodiments, the method comprises: a. grinding the at least one active ingredient to form an at least one active ingredient powder; b. mixing *quillaja* extract with water to form the *quillaja* extract solution; mixing the at least one active ingredient powder with *quillaja* extract solution to form a mixture comprising the at least one active ingredient powder and the *quillaja* extract; drying the mixture comprising the at least one active ingredient powder and the *quillaja* extract by stirring or by spray drying to form a dried solid comprising the least one active ingredient powder and the *quillaja* extract; and e. grinding the solid comprising the least one active ingredient powder and the *quillaja* extract to form the powder comprising *quillaja* extract and the at least one active ingredient.

In addition to the embodiments provided for herein, in some embodiments, the compositions described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes (such as eye drop), or intravaginal, by inhalation, by depot injections, by aerosol spray, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer compositions comprising one or more active ingredients, locally to an area in need of treatment. This may be achieved, for example, and not by way of limitation, by topical application, e.g., in conjunction with a wound dressing after surgery.

The compositions described herein can be administered either alone or in combination (concurrently or serially) with other compositions, such as but not limited to pharmaceuticals, other dietary ingredients or nutritional supplements.

The methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of composition to be administered can be an amount, which is effective. The dosage to be administered will depend on the characteristics of the subject being treated, e.g., the particular animal treated, age, weight, health, types of concurrent treatment, if any, and frequency of treatments, and can be easily determined by one of skill in the art. The standard dosing can be used and adjusted (i.e., increased or decreased) depending upon the factors described herein. The selection of the specific dose regimen can be selected or adjusted or titrated by the one of skill in the according to methods known to one of skill in the art to obtain the desired response.

The amount of compositions described herein that will be effective in the treatment and/or prevention of a particular disease, condition, or disorder or to support the health and well-being of a subject will depend on the nature and extent of the disease, condition, or disorder, and the subject and can be determined by standard techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each subject's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight. The composition can also have the ratios and percentages of the active ingredients provided for herein.

In some embodiments, suitable dosage ranges for intravenous (i.v.) administration are from about 0.01 mg to about 100 mg per kg body weight, from about 0.1 mg to about 50 mg per kg body weight, or from about 1 mg to about 10 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 10 mg per kg of body weight. Effective doses may be extrapolated from dose-response curves derived from in vitro or animal model test systems. Such animal models and systems are well known in the art. The composition can also have the ratios and percentages of the active ingredients provided for herein.

The compositions described herein can be formulated for parenteral administration by injection, such as by bolus injection or continuous infusion. The compositions can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compositions described herein can be formulated with pharmaceutically acceptable carriers well known in the art. Such carriers enable the compositions to be formulated as tablets, pills, dragees, capsules, emulsions, liquids, gels (e.g. softgels), syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores.

Orally administered compositions can contain one or more optional agents, for example, sweetening agents such as allulose, fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period. Selectively permeable membranes surrounding an osmotically active driving compound are also suitable for orally administered compositions. Oral compositions can include standard vehicles such as mannitol, lactose, starch, magnesium stearate, sodium saccharine, cellulose, magnesium carbonate, etc. Such vehicles are suitably of food or pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compositions can also be formulated as food, such as those foods described herein.

Pharmaceutical preparations, which can be used orally, include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compositions described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, such as gelatin for use in an inhaler or insufflator can be formulated containing a powder mix of an active ingredient and a suitable powder base such as lactose or starch.

The compositions described herein can also be formulated in rectal compositions such as suppositories or retention enemas, such as containing conventional suppository bases such as cocoa butter or other glycerides. The compositions described herein can also be formulated in vaginal compositions such as vaginal creams, suppositories, douche, pessaries, vaginal rings, and intrauterine devices.

In transdermal administration, the compositions can be applied to a plaster, or can be applied by transdermal, therapeutic systems that are consequently supplied to the organism. In some embodiments, the compositions are present in creams, solutions, powders, fluid emulsions, fluid suspensions, semi-solids, ointments, pastes, gels, jellies, and foams, or in patches containing any of the same.

The compositions described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

In some embodiments, the compositions can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compositions described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compositions can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compositions described herein can be used with agents including, but not limited to, topical analgesics (e.g., lidocaine), barrier devices (e.g., GelClair), or rinses (e.g., Caphosol).

In some embodiments, the compositions described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.).

In some embodiments, the formulation can be lyophilized to a solid and reconstituted with, for example, water prior to use.

When administered to a mammal (e.g., to an animal for veterinary use or to a human for clinical use) the compositions can be administered in isolated form.

When administered to a human, the compositions can be sterile. Water is a suitable carrier when the composition as described herein is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, and capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compositions are formulated in accordance with routine procedures as a pharmaceutical composition adapted for administration to humans Typically, compositions are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition as described herein is to be administered by infusion, it can be dispensed, for example, with an infusion bottle containing sterile pharmaceutical grade water or saline. Where the composition as described herein is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid or ester (such as ascorbyl palmitate), or sorbic acid, or other agents know to those of skill in the art. Such preservatives are typically employed at a level of from about 0.001% to about 1.0% by weight.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In some embodiments, the composition optionally contains a suspending agent. For example, in those embodiments in which the composition is an aqueous suspension or solution/suspension, the composition can contain one or more polymers as suspending agents such as beeswax and natural gums. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, sodium citrate, and sodium bicarbonate. Such acids, bases and buffers are included in an amount required to maintain pH of the composition in an acceptable range.

One or more acceptable salts, solvates or prodrugs can be included in the compositions in an amount required to bring osmolality of the composition into an acceptable range. Such salts include, but are not limited to, those having sodium cation and chloride, citrate, or ascorbate anions. In some embodiments, the salt is sodium chloride.

In some embodiments, packs or kits comprising one or more containers filled with one or more compositions described herein are provided. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one composition described herein. In some embodiments, the kit comprises a composition described herein in a single injectable dosage form, such as a single dose within an injectable device such as a syringe with a needle. In some embodiments, the pack or kit comprises a desiccant to control the humidity of the package.

In some embodiments, the methods comprise administering to the subject one or more compositions described herein. In some embodiments, the subject is a subject in need of such treatment. As described herein, in some embodiments, the subject is a mammal, such as, but not limited to, a human.

In some embodiments, also provided are one or more compositions described above, or a pharmaceutically acceptable salt, solvate or prodrug thereof, for use in the manufacture of a medicament having utility in an application described herein can be used in co-therapy, co-administration or co-formulation with a composition as described above. Therefore, the compositions described herein can be administered either before, concurrently with, or after such therapeutics are administered to a subject.

The additional medicament can be administered in co-therapy (including co-formulation) with the one or more of the compositions described herein.

The present disclosure also provides the following non-limiting embodiments:

In order that the embodiments disclosed herein may be more efficiently understood, examples are provided below. It should be understood that these examples are for illustrative purposes only and are not to be construed as limiting the embodiments in any manner.

In some embodiments, the following embodiments are provided:

1. A composition comprising *quillaja* extract and at least one active ingredient.
2. The composition of embodiment 1, wherein the active ingredient is lipid soluble.
3. The composition of embodiment 1, wherein the active ingredient is selected from the group consisting of a nutritional supplement, a dietary ingredient, a medicine, and a food additive.
4. The composition of embodiment 3, wherein the nutritional supplement or dietary ingredient is a quinone, a pyrroloquinoline quinone (PQQ), a cannabinoid, a *curcuma* isolate, berberine, diindolylmethane (DIM), a phenolic, a lipid-soluble vitamin, a symmetrical carotenoids, an omega-3 fatty acid, or a terpenoid, or any combination thereof.

5. The composition of embodiment 3, wherein the nutritional supplement or dietary ingredient is CoQ10, reduced CoQ10, oxidized CoQ10, vitamin K-2, cannabidiol, tetrahydrocannabinol, tumerone, curcumene, xanthorrhizol, curcumin, berberine, diindolylmethane (DIM), resveratrol, quercetin, Vitamin A, Vitamin D, Vitamin E, Vitamin K, beta-carotene, zeaxanthin, lycopene, astaxanthin, an omega-3 fatty acid, a monoterpenoid, a di-terpenoid, a tri-terpenoid, or a sesquiterpenoid, or any combination thereof.

6. The composition of embodiment 4, wherein the dietary ingredient is CoQ10, reduced CoQ10, oxidized CoQ10, menaquinone, curcumin, berberine, diindolylmethane (DIM), resveratrol, or quercetin, or any combination thereof.

7. The composition of embodiment 1, wherein the active ingredient is CoQ10.

8. The composition of embodiment 7, wherein the CoQ10 is ubiquinol, ubiquinone, or a mixture of ubiquinol and ubiquinone.

9. The composition of embodiment 8, wherein the CoQ10 is a mixture of ubiquinol and ubiquinone and wherein the ubiquinol is less than 95% by weight in the mixture.

10. The composition of embodiment 1, wherein the weight ratio of the *quillaja* extract to the active ingredient is from about 12:75 to about 75:25.

11. The composition of embodiment 1, wherein the weight ratio of the *quillaja* extract to the active ingredient is about 12:75, about 25:75, about 40:60, about 50:50, about 67:33, or about 75:25.

12. The composition of any one of embodiments 1-11, wherein the composition is in a form of soft capsule, hard capsule, tablet, gel capsule, softgel, 2-piece liquid-filled capsule, bar, confectionary, chocolate, powder, oral suspension, pill, hard-shell, truffle, ganache, truffle ganache, gum, chewable form, an effervescent packet or pouch, an eye drop, or an aerosol spray.

13. The composition of embodiment 12, wherein the form is a gel capsule, soft capsule, a hard capsule, or a tablet.

14. The composition of any one of embodiments 1-13, wherein the *quillaja* extract contains about 20% to about 30% of *quillaja* saponin by weight.

15. The composition of any one of embodiments 1-14, wherein the composition further comprises at least one triglyceride, at least one phospholipid, or a combination thereof.

16. The composition of embodiment 15, wherein the triglyceride is a medium-chain triglyceride (MCT).

17. The composition of embodiment 14, wherein the phospholipid is a lecithin.

18. A method of increasing bioaccessibility and/or bioavailability of the active ingredient of any one of embodiments 1-17 in a subject, the method comprising administering the composition of any one of embodiments 1-17 to the subject.

19. The method of embodiment 18, wherein the method comprising administering the composition by parenteral, subcutaneous, intravenous, intramuscular, intraperitoneal, transdermal, oral, buccal, sublingual, ocular, or intravaginal administration, by inhalation, by depot injections, or by implants.

20. The method of embodiment 19, wherein the method comprising administering the composition by oral administration.

21. The method of embodiment 19, wherein the method comprising administering the composition by ocular administration.

22. The method of any one of embodiments 18-20, wherein the bioaccessibility of the active ingredient increases by about 200%.

23. The method of embodiment 22, wherein the weight ratio of the *quillaja* extract to the active ingredient is about 12:75.

24. The method of embodiments 22 or 23, wherein the at least one active ingredient is CoQ10.

25. The composition of embodiment 24, wherein the CoQ10 is ubiquinol, ubiquinone, or a mixture of ubiquinol and ubiquinone.

26. The composition of embodiment 24, wherein the CoQ10 is a mixture of ubiquinol and ubiquinone and wherein the ubiquinol is less than 95% by weight in the mixture.

27. The method of any one of embodiments 18-25, wherein at least one active ingredient is quercetin.

28. The method of any one of embodiments 17-27, wherein the subject is the subject in need thereof.

29. A method of preparing the composition of any one of embodiments 1-17, the method comprising mixing *quillaja* extract with the at least one active ingredient.

30. The method of embodiment 29, further comprising incorporating the composition into a gel capsule.

31. A method of preparing a powder comprising *quillaja* extract and at least one active ingredient, the method comprising drying a solution comprising *quillaja* extract and at least one active ingredient to form a dried solid and grinding the solid to form a powder comprising *quillaja* extract and the at least one active ingredient.

32. The method of embodiment 31, wherein the drying is performed by spray drying.

33. The method of embodiment 31, wherein the drying is performed by stirring until the solution is dried.

34. The method of any one of embodiments 31-33, wherein the dried solid is a fully dried solid.

35. The method of any one of embodiments 31-34, wherein the method further comprises making a solution comprising *quillaja* extract and at least one active ingredient by mixing a *quillaja* extract solution with at least one active ingredient.

36. The method of embodiment 35, wherein the at least one active ingredient mixed with the *quillaja* extract solution is a solid.

37. The method of embodiment 36, wherein the at least one active ingredient solid is a powder.

38. The method of embodiment 37, wherein the method further comprises grinding the at least one active ingredient to form the powder.

39. The method of embodiment 35, further comprising preparing the *quillaja* extract solution.

40. The method of embodiment 39, wherein preparing the *quillaja* extract solution comprises mixing *quillaja* extract in water to form the *quillaja* extract solution.

41. The method of any one of embodiments 31-40, further comprising preparing a gel capsule comprising the powder comprising *quillaja* extract and the at least one active ingredient.

42. The method of any one of embodiments 31-41, wherein the method comprises:
 a. grinding the at least one active ingredient to form an at least one active ingredient powder;

b. mixing *quillaja* extract with water to form the *quillaja* extract solution;

c. mixing the at least one active ingredient powder with *quillaja* extract solution to form a mixture comprising the at least one active ingredient powder and the *quillaja* extract;

d. drying the mixture comprising the at least one active ingredient powder and the *quillaja* extract by stirring or by spray drying to form a dried solid comprising the least one active ingredient powder and the *quillaja* extract; and e. grinding the solid comprising the least one active ingredient powder and the *quillaja* extract to form the powder comprising *quillaja* extract and the at least one active ingredient.

EXAMPLES

Example A1: Preparation of Compositions by Mixing Active Ingredient and *Quillaja* Powder at Fixed Ratios by Weight and Testing the Dispersibilities of the Compositions This example sets forth compositions and methods for making compositions of one active ingredient with *quillaja* powder. Each of the compositions is prepared by mixing one active ingredient with *quillaja* powder at a fixed ratio of about 75:25, about 60:40, about 50:50, about 40:60, or about 25:75. This example also sets forth methods to test the dispersibilities of the resulting compositions.

Procedure:
1. Add 5 mL DI water to 15 mL disposable glass test tube
2. Weight out Active ingredient (back weigh for accuracy)
   a. For 100% active ingredient, weigh out close to the target amount, note the weight, then zero the balance (with active ingredient still on it)
   b. Add active ingredient to test tube with DI water
   c. Place mostly empty powder weight boat back onto scale and record actual weight added
   d. For other mixtures of active ingredient and *quillaja* powder, perform similar but add to new weight boat to mix powders (instead of adding directly to test tube)
3. Weigh out *quillaja* powder (back weigh for accuracy)
   a. Weigh out close to target amount of *quillaja*, note the weight, then zero the balance (with *quillaja* still on it)
   b. Add *quillaja* to mixture weight boat (with active)
   c. Place mostly empty *quillaja* weigh boat back onto scale and record actual weight added
4. Repeat for all ratios of powder mixtures below (dose-dependent study):

| (g) | % Active | | | | | |
|---|---|---|---|---|---|---|
| | 25% | 40% | 50% | 60% | 75% | 100% |
| Active | 0.0750 | 0.0750 | 0.0750 | 0.0750 | 0.0750 | 0.0750 |
| Quillaja | 0.2250 | 0.1125 | 0.0750 | 0.0500 | 0.0250 | 0.0000 |

5. Mix powders together
6. Add powder mixture to the test tube with DI water. Vortex for exactly 2 minutes and perform time-dependent study
7. Let settle for 10 minutes then take picture/note observations such as degree of turbidity, dispersibility, any large solids, etc.
8. After 30 minutes (total), take picture/note observations
9. After 2 hours (total), take picture/note observations
10. After 4 hours (total), take picture/note observations
11. Take special note of the size of the solid "pellet" that settles out on the bottom
    a. Try to measure its size (estimated) by taking the radius/diameter combined with the height Example A2: Preparation of Compositions by Mixing CoQ10 Powder and *Quillaja* Powder in Fixed Ratios and Testing the Dispersibilities of the Compositions This example sets forth compositions of CoQ10 powder and *quillaja* powder at fixed ratios of 100:0, about 75:25, about 60:40, about 50:50, about 40:60, and about 25:75 respectively. As used herein in Example A2, CoQ10 powder is ubiquinone powder as CoQ10(ubiquinone) powder. The compositions have been prepared according to experimental procedures in Example 1A. A time-dependent trial of sedimentation rates of the compositions comprising ubiquinone powder and *quillaja* powder at different ratios in water was conducted at time points of 10 minutes, 30 minutes, 2 hours, and 4 hours are shown in FIG. 1. Regarding the test tubes in each of the pictures of FIG. 1, from right to left, the weight ratios of CoQ10(ubiquinone) powder to *quillaja* powder are in the order of 100:0, about 75:25, about 60:40, about 50:50, about 40:60, and about 25:75 respectively. The tube without *quillaja* powder showed complete separation of clear water and ubiquinone powder, indicating the lowest solubility. Increasing extent of turbidity was indicative of the highest dispersibility and solubility. Increasing the weight ratio of *quillaja* powder to ubiquinone powder increases the dispersibility and solubility of active powder in water.

Figure 2:
FIG. 2 illustrates dispersibilities of certain compositions comprising curcumin powder and *quillaja* extract in certain ratios.
Figure 2:
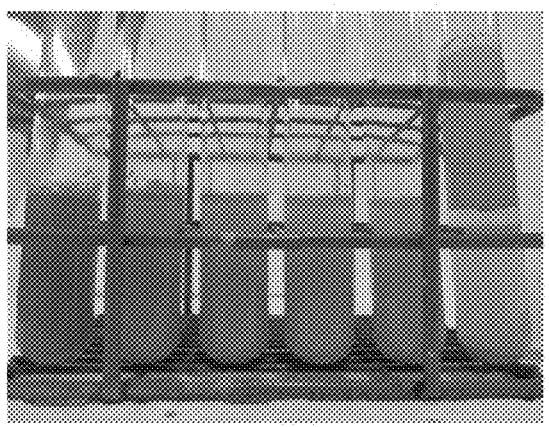
Figure 2:
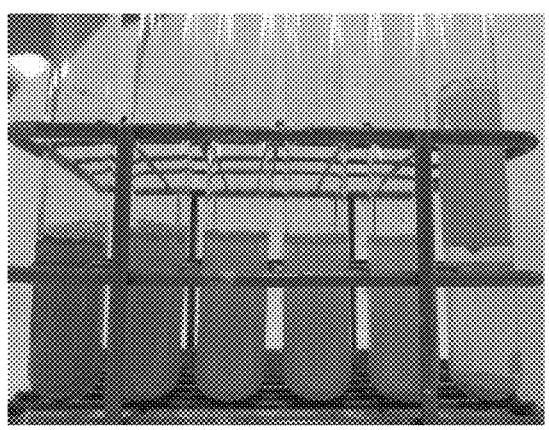
Figure 2:
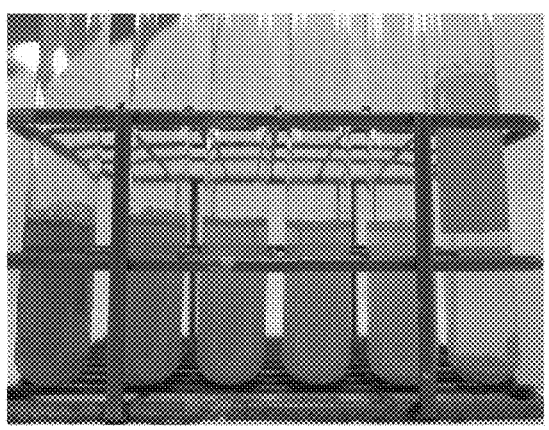

Example A3: Preparation of Compositions by Mixing Curcumin Powder and *Quillaja* Powder in Fixed Ratios and Testing the Dispersibilities of the Compositions This example sets forth compositions of curcumin powder and *quillaja* powder at fixed ratios of about 75:25, about 60:40, about 50:50, about 40:60, and about 25:75 respectively. The compositions have been prepared according to experimental procedures in Example 1A. A time-dependent trial of sedimentation rates of the compositions comprising curcumin powder and *quillaja* powder at different ratios in water was conducted at time points of 10 minutes, 30 minutes, 2 hours, and 4 hours are shown in FIG. 2. Regarding the test tubes in each of the pictures of FIG. 2, from right to left, the weight ratios of curcumin powder to *quillaja* powder are in the order of 100:0, about 75:25, about 60:40, about 50:50, about 40:60, and about 25:75 respectively. The tube without *quillaja* powder showed complete separation of clear water and ubiquinone powder, indicating the lowest solubility. Increasing extent of turbidity was indicative of the highest dispersibility and solubility. Increasing the weight ratio of *quillaja* powder to ubiquinone powder increases the dispersibility and solubility of active powder in water.

Figure 3:
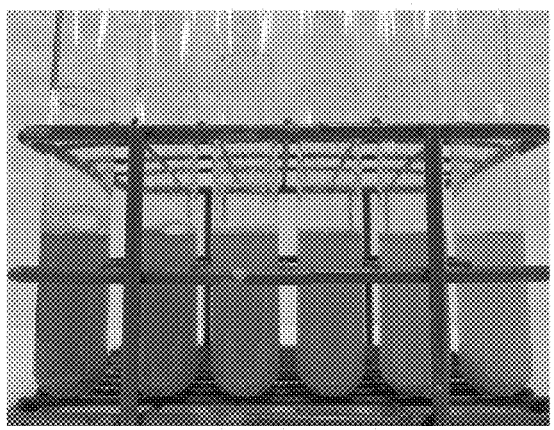
FIG. 3 illustrates dispersibilities of certain compositions comprising berberine powder and *quillaja* extract in certain ratios.
Figure 3:
Figure 3:
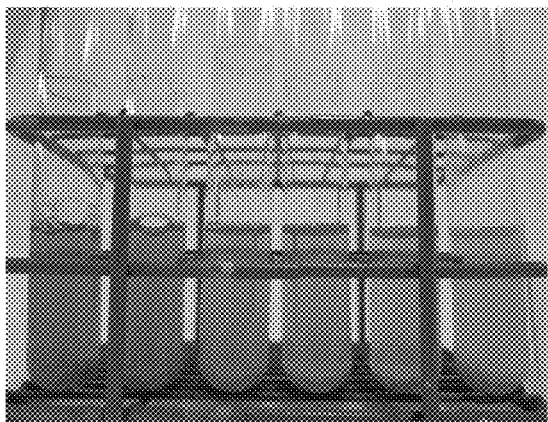
Figure 3:
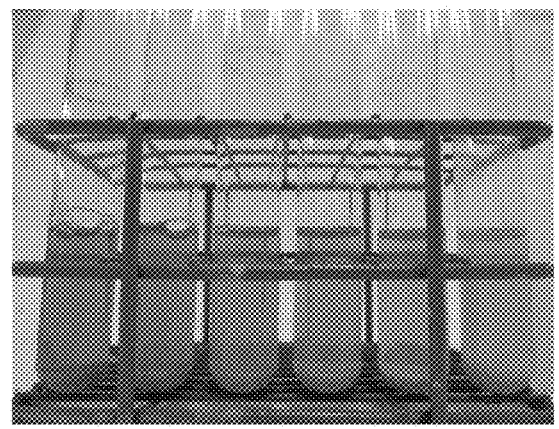

Example A4: Preparation of Compositions by Mixing Berberine Powder and *Quillaja* Powder in Fixed Ratios and Testing the Dispersibilities of the Compositions This example sets forth compositions of berberine powder and *quillaja* powder at fixed ratios of about 75:25, about 60:40, about 50:50, about 40:60, and about 25:75 respectively. The compositions have been prepared according to experimental procedures in Example 1A. A time-dependent trial of sedimentation rates of the compositions comprising berberine powder and *quillaja* powder at different ratios in water was conducted at time points of 10 minutes, 30 minutes, 2 hours, and 4 hours are shown in FIG. 3. Regarding the test tubes in each of the pictures of FIG. 3, from right to left, the weight ratios of berberine powder to *quillaja* powder are in the order of 100:0, about 75:25, about 60:40, about 50:50, about 40:60, and about 25:75 respectively. The tube without *quillaja* powder showed complete separation of clear water and ubiquinone powder, indicating the lowest solubility. Increasing extent of turbidity was indicative of the highest dispersibility and solubility. Increasing the weight ratio of *quillaja* powder to ubiquinone powder increases the dispersibility and solubility of active powder in water.

Figure 4:
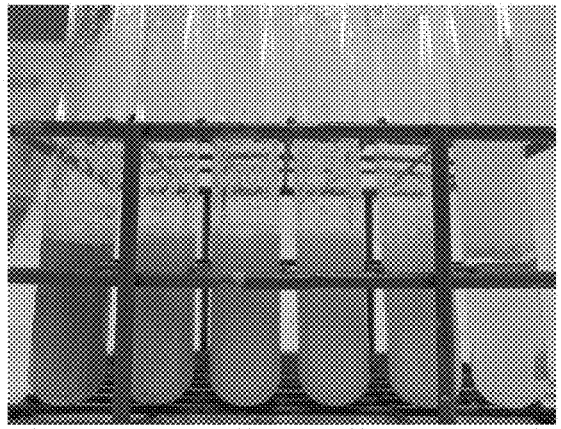
FIG. 4 illustrates dispersibilities of certain compositions comprising diindolylmethane (DIM) powder and *quillaja* extract in certain ratios.
Figure 4:
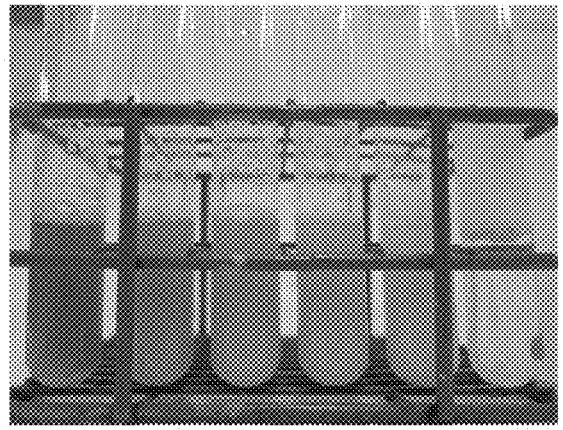
Figure 4:
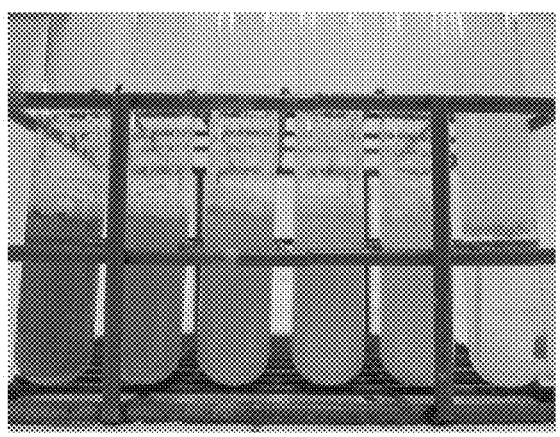
Figure 4:
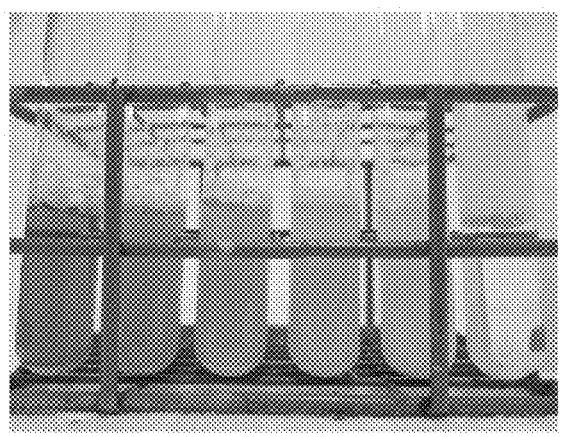

Example A5: Preparation of Compositions by Mixing Diindolylmethane (DIM) Powder and *Quillaja* Powder in Fixed Ratios and Testing the Dispersibilities of the Compositions This example sets forth compositions of DIM powder and *quillaja* powder at fixed ratios of about 75:25, about 60:40, about 50:50, about 40:60, and about 25:75 respectively. The compositions have been prepared according to experimental procedures in Example 1A. A time-dependent trial of sedimentation rates of the compositions comprising diindolylmethane powder and *quillaja* powder at different ratios in water was conducted at time points of 10 minutes, 30 minutes, 2 hours, and 4 hours are shown in FIG. 4. Regarding the test tubes in each of the pictures of FIG. 4, from right to left, the weight ratios of diindolylmethane powder to *quillaja* powder are in the order of 100:0, about 75:25, about 60:40, about 50:50, about 40:60, and about 25:75 respectively. The tube without *quillaja* powder showed complete separation of clear water and ubiquinone powder, indicating the lowest solubility. Increasing extent of turbidity was indicative of the highest dispersibility and solubility. Increasing the weight ratio of *quillaja* powder to ubiquinone powder increases the dispersibility and solubility of active powder in water.

Figure 5:
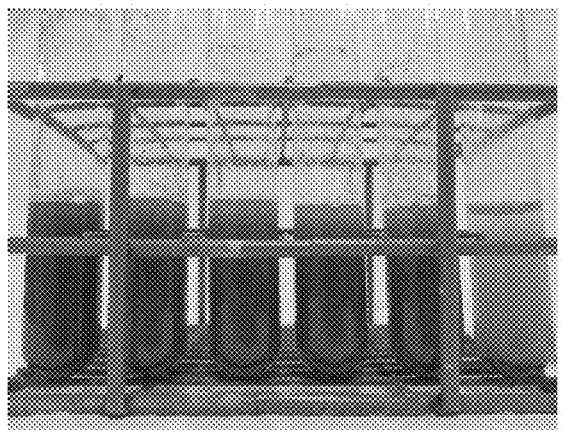
FIG. 5 illustrates dispersibilities of certain compositions comprising resveratrol powder and *quillaja* extract in certain ratios.
Figure 5:
Figure 5:
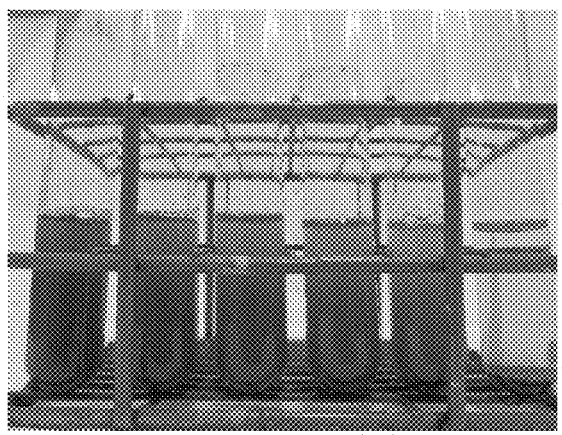
Figure 5:

Example A6: Preparation of Compositions by Mixing Resveratrol Powder and *Quillaja* Powder in Fixed Ratios and Testing the Dispersibilities of the Compositions This example sets forth compositions of resveratrol powder and *quillaja* powder at fixed ratios of about 75:25, about 60:40, about 50:50, about 40:60, and about 25:75 respectively. The compositions have been prepared according to experimental procedures in Example 1A. A time-dependent trial of sedimentation rates of the compositions comprising resveratrol powder and *quillaja* powder at different ratios in water was conducted at time points of 10 minutes, 30 minutes, 2 hours, and 4 hours are shown in FIG. 5. Regarding the test tubes in each of the pictures of FIG. 5, from right to left, the weight ratios of resveratrol powder to *quillaja* powder are in the order of 100:0, about 75:25, about 60:40, about 50:50, about 40:60, and about 25:75 respectively. The tube without *quillaja* powder showed complete separation of clear water and ubiquinone powder, indicating the lowest solubility. Increasing extent of turbidity was indicative of the highest dispersibility and solubility. Increasing the weight ratio of *quillaja* powder to ubiquinone powder increases the dispersibility and solubility of active powder in water.

Figure 6:
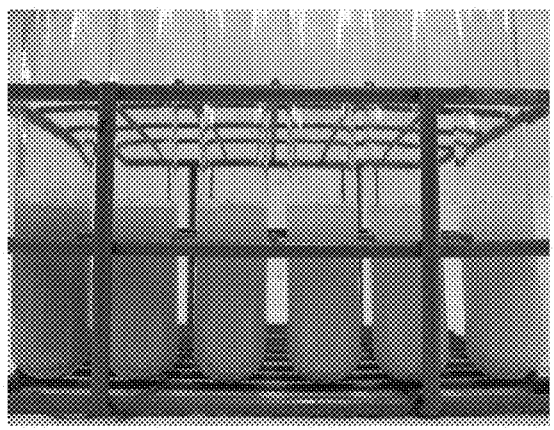
FIG. 6 illustrates dispersibilities of certain compositions comprising quercetin powder and *quillaja* extract in certain ratios.
Figure 6:
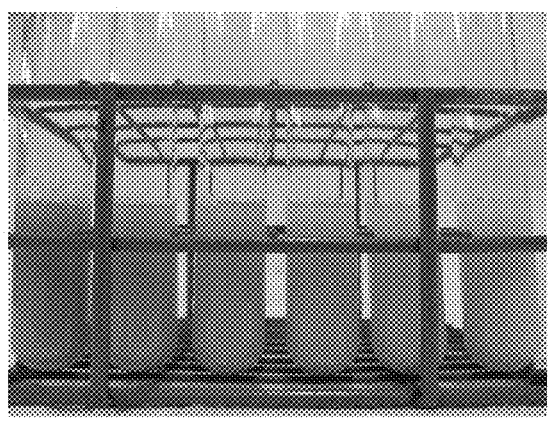
Figure 6:
Figure 6:
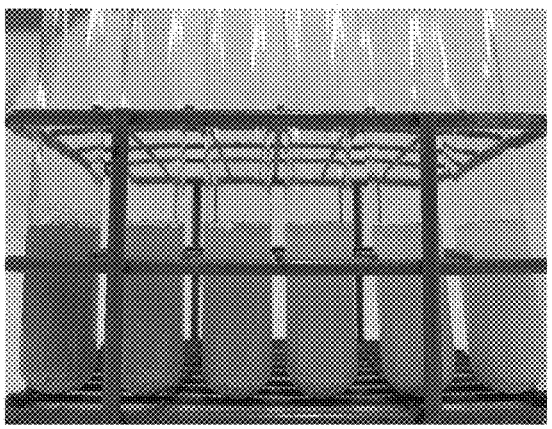

Example A7: Preparation of Compositions by Mixing Quercetin Powder and *Quillaja* Powder in Fixed Ratios and Testing the Dispersibilities of the Compositions This example sets forth compositions of quercetin powder and *quillaja* powder at fixed ratios of about 75:25, about 60:40, about 50:50, about 40:60, and about 25:75 respectively. The compositions have been prepared according to experimental procedures in Example 1A. A time-dependent trial of sedimentation rates of the compositions comprising quercetin powder and *quillaja* powder at different ratios in water was conducted at time points of 10 minutes, 30 minutes, 2 hours, and 4 hours are shown in FIG. 6. Regarding the test tubes in each of the pictures of FIG. 6, from right to left, the weight ratios of quercetin powder to *quillaja* powder are in the order of 100:0, about 75:25, about 60:40, about 50:50, about 40:60, and about 25:75 respectively. The tube without *quillaja* powder showed complete separation of clear water and ubiquinone powder, indicating the lowest solubility. Increasing extent of turbidity was indicative of the highest dispersibility and solubility. Increasing the weight ratio of *quillaja* powder to ubiquinone powder increases the dispersibility and solubility of active powder in water.

Example A8: Relative Dispersibilities of Various Active Ingredients in *Quillaja* Powder This example sets forth comparisons of the dispersibilities for compositions of Examples A2-A7, which comprise various active ingredients mixed with *quillaja* powder at various fixed ratios. After comparing the results shown in FIGS. 1-6, the relative dispersibilities are as following:
a) Relative Dispersibilities without *quillaja* powder: Quercetin>Berberine>Resveratrol>Curcumin>DIM>CoQ10 (ubiquinone)
b) Relative Dispersibilities with *quillaja* powder at time point of 30 minute or less: Quercetin>(Curcumin=Resveratrol)>(DIM=Berberine)>CoQ10 (ubiquinone)
c) Relative Dispersibilities with *quillaja* powder at time point of 2 hours or more Quercetin>(DIM=Curcumin=Resveratrol)>Berberine>CoQ10 (ubiquinone)

Example A9: Surface Tension Interactions of Example A2-A7

This example sets forth comparisons of the surface tension interactions of the compositions of Example A2-A7. The surface tension interactions of the compositions of various active ingredients mixed with *quillaja* powder at various fixed ratios were specifically compared with those of the compositions of various active ingredients without *quillaja* powder. Surface tension interaction is determined by visual observation of glass smearing of active ingredient powders above the water level.
a) Relative surface tension interaction without *quillaja* powder: (CoQ10(ubiquinone)≥Curcumin)>(Resveratrol≥DIM)>(Quercetin≥Berberine)
b) Relative surface tension interaction with *quillaja* powder:

All active ingredient powders were practically the same indicating *quillaja* powder reducing surface tension and increasing water solubility. Highest surface tension without *quillaja* powder indicates maximum water insolubility of the experimented list of examples. This means CoQ10(ubiquinone) and curcumin, as shown in FIGS. 1-2. Lowest surface tension without *quillaja* powder indicates "best" water solubility of the experimented list of examples. This means quercetin and berberine, as shown in FIG. 6 and FIG. 3.

Example B1: Preparation of Compositions by Mixing Various Active Ingredients with *Quillaja* Powder Solutions and Testing the Dispersibilities of the Compositions This example sets forth compositions and methods for making compositions comprising one active ingredient and *quillaja* powder. Each of the compositions is prepared according to the procedure below as described herein, wherein the weight ratio of the *quillaja* powder to the active ingredient is about 75:25, about 50:50, about 33:67, or about 25:75. This example also sets forth methods to test the dispersibilities of the resulting compositions.

Procedure:
1. Grind active to fine powder before weighing
2. Measure out *quillaja* powder amount (as listed in table below) and dissolve into matching amount of water in a small beaker
3. Weigh out listed amount of ground active and mix into matching *quillaja* solution

|   | Active:Quillaja | Active (g) | Quillaja (g) | DI H2O (mL) |
|---|---|---|---|---|
| 1 | 0:100 | 0.0000 | 1.5000 | 2.25 |
| 2 | 25:75 | 0.5000 | 1.5000 | 3.00 |
| 3 | 33:67 | 0.5000 | 1.0000 | 2.25 |
| 4 | 50:50 | 0.5000 | 0.5000 | 1.50 |
| 5 | 75:25 | 0.5000 | 0.2500 | 1.125 |

4. Once fully mixed in, dry in open air or on low heat stir plate until thoroughly dry
    a. Use a glass rod to stir every so often for even drying
5. Scrape off all solids left inside and grind into a fine powder
6. Test solubility (appearance, turbidity, and settling)
    a. Following amounts are listed to add 0.0300 g (30 mg) active to 100 mL water to simulate similar concentrations in the stomach
    b. Add the following weights (corresponding to sample #'s in step 3) to 100 mL DI water

|   | 1 | 2 | 3 | 4 | 5 |
|---|---|---|---|---|---|
| (g) | 0.0900 | 0.1200 | 0.0900 | 0.0600 | 0.0400 |

7. Check samples (appearance, turbidity, and settling) and take notes/observations/pictures at:
    a. 10 min, 30 min, 2 hours, and 4 hours Example C1: Relative Dispersibilities of Lipid-Soluble Powders in *Quillaja* and Guar Gum This example sets forth compositions and methods for making compositions comprising one active ingredient, *quillaja* powder, and guar gum. The compositions described herein are expected to be prepared according to the procedure as described in Example B1. Dispersibilities of the compositions described herein are expected to be tested according to the procedure as described in Example B1.

Example C2: Relative Dispersibilities of Lipid-Soluble Powders in *Quillaja* and Acacia Gum This example sets forth compositions and methods for making compositions comprising one active ingredient, *quillaja* powder, and acacia gum. The compositions described herein are expected to be prepared according to the procedure as described in Example B1. Dispersibilities of the compositions described herein are expected to be tested according to the procedure as described in Example B1.

Example C3: Relative Dispersibilities of Lipid-Soluble Powders in *Quillaja* and Locust Bean Gum This example sets forth compositions and methods for making compositions comprising one active ingredient, *quillaja* powder, and locust bean gum. The compositions described herein are expected to be prepared according to the procedure as described in Example B1. Dispersibilities of the compositions described herein are expected to be tested according to the procedure as described in Example B1.

Example D1: Relative Dispersibilities of Lipid-Soluble Powders in Glycerides (Mono-, Di-, and Tri-Glycerides)

This example sets forth compositions and methods for making compositions comprising one active ingredient, *quillaja* powder, and glycerides (mono-, di-, and tri-glycerides). The compositions described herein are expected to be prepared according to the procedure as described in Example B1. Dispersibilities of the compositions described herein are expected to be tested according to the procedure as described in Example B1.

Example D2: Relative Dispersibilities of Lipid-Soluble Powders in Glycerides (Mono-, Di-, and Tri-Glycerides) and Maltodextrins This example sets forth compositions and methods for making compositions comprising one active ingredient, *quillaja* powder, glycerides (mono-, di-, and tri-glycerides), and maltodextrins. The compositions described herein are expected to be prepared according to the procedure as described in Example B1. Dispersibilities of the compositions described herein are expected to be tested according to the procedure as described in Example B1.

Example E1: Relative Dispersibilities of Lipid-Soluble Powders in *Quillaja* and Guar Gum This example sets forth compositions and methods for making compositions comprising one active ingredient, *quillaja* powder, and guar gum. The compositions described herein are expected to be prepared according to the procedure as described in Example B1. Dispersibilities of the compositions described herein are expected to be tested according to the procedure as described in Example B1.

Example F1: Effect of *Quillaja* Powder on Bioaccessibility of Ubiquinol

This example sets forth to test the effect of *quillaja* powder on bioaccessiblity of ubiquinol. Bioaccessibility of ubiquinol was measured by simulated in vitro digestion. Briefly, samples were weighed out and mixed with 10 mL saliva solution and 0.3 g mucin. The mixture was incubated under 37° C., 300-400 rpm for 10 min 20 mL of Fasted State Simulated Gastric Fluid (FASSGF) and 0.64 g of pepsin was then added to the mixture. After adjusting pH to 2.6, mixture was incubated under 37° C., 300-400 rpm for 2 hours. The mixture was transferred to the chamber of 916 Ti-Touch, where pH can be maintained at 7.0. 20 mL of Fasted State Simulated Intestinal Fluid (FASSIF), 4 mL of bile extract solution (5 mg/mL), and 2.5 mL of lipase solution (4.8 mg/mL) were added to the mixture. After 2-hour incubation at 37° C., the mixture was centrifuged at10000 rpm under 4° C. Supernatant was filtered with 0.22 µM filter, and then subjected for HPLC analysis. Bioaccessibility (%)=(ubiquinol measured by HPLC/theoretical amount of ubiquinol in the sample)×100%.

Figure 7:
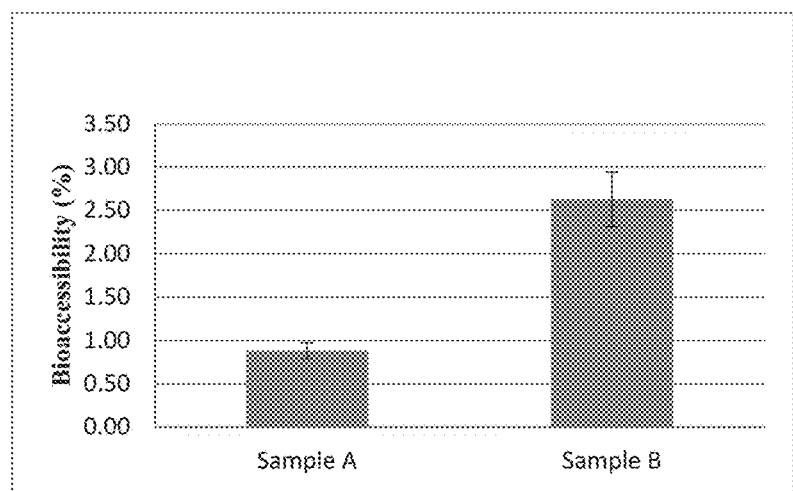
FIG. 7 illustrates the increase in bioaccessibility of a composition comprising a *quillaja* extract and ubiquinol.

Results:

The ubiquinol by itself has a bioaccessibility of 0.88% (sample A). Surprisingly and unexpectedly, addition of quillaja powder (sample B) increases bioaccessibility of ubiquinol by about 200%. See the results in FIG. 7. This increase in bioaccessibility by the addition of a quillaja powder could not have been predicted and was surprising.

Example G1: Effect of *Quillaja* Powder on Bioavailability of Berberine in Human This example sets forth to test the effect of quillaja powder on bioavailability of berberine in Huma. The effects of quillaja powder and on the bioavailability of orally ingested berberine in human volunteers was investigated. Subjects were randomized to either receive a single dose of powder berberine or quillaja-functionalized berberine. Blood plasma concentration of berberine was analyzed at different time points.

Surprisingly and unexpectedly, quillaja powder was found to increase the bioavailability of orally ingested berberine in human volunteers and the bioavailability of quillaja-emulsified berberine was significantly higher than the berberine powder by itself.

The embodiments and examples provided herein demonstrate the ability to use quillaja powder to increase the bioaccessiblity of active ingredients, such as dietary ingredients, including, but not limited to those provided for herein and, for example, ubiquinol, ubiquinone, or the mixture of ubiquinone and ubiquinol, berberine, quercetin, and other active ingredients. Without being bound to any particular theory, the increase in bioaccessiblity is due to the ability of the quillaja extract to increase the dispersion of the active ingredient and decrease the surface tension. These results would not have been expected or predicted.

While the compounds described herein have been described with reference to examples, those skilled in the art recognize that various modifications may be made without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

What is claimed is:

1. A composition comprising *quillaja* extract and at least one active ingredient, wherein the weight ratio of the *quillaja* extract to the active ingredient is from 12:75 to 75:25 or from 25:75 to 75:25.

2. The composition of claim 1, wherein the active ingredient is lipid soluble.

3. The composition of claim 1, wherein the active ingredient is selected from the group consisting of a nutritional supplement, a dietary ingredient, a medicine, and a food additive.

4. The composition of claim 3, wherein the nutritional supplement or dietary ingredient is a quinone, a pyrroloquinoline quinone (PQQ), a cannabinoid, a *curcuma* isolate, berberine, diindolylmethane (DIM), a phenolic, a lipid-soluble vitamin, a symmetrical carotenoids, an omega-3 fatty acid, a terpenoid, or any combination thereof.

5. The composition of claim 3, wherein the nutritional supplement or dietary ingredient is CoQ10, reduced CoQ10, oxidized CoQ10, vitamin K-2, cannabidiol, tetrahydrocannabinol, tumerone, curcumene, xanthorrhizol, curcumin, berberine, diindolylmethane (DIM), resveratrol, quercetin, Vitamin A, Vitamin D, Vitamin E, Vitamin K, beta-carotene, zeaxanthin, lycopene, astaxanthin, an omega-3 fatty acid, a mono-terpenoid, a di-terpenoid, a tri-terpenoid, a sesqui-terpenoid, or any combination thereof.

6. The composition of claim 1, wherein the active ingredient is CoQ10.

7. The composition of claim 6, wherein the CoQ10 is ubiquinol, ubiquinone, or a mixture of ubiquinol and ubiquinone.

8. The composition of claim 1, wherein the composition is in a form of soft capsule, hard capsule, tablet, gel capsule, softgel, 2-piece liquid-filled capsule, bar, confectionary, chocolate, powder, oral suspension, pill, hard-shell, truffle, ganache, truffle ganache, gum, chewable form, an effervescent packet or pouch, an eye drop, or an aerosol spray.

9. The composition of claim 1, wherein the *quillaja* extract contains about 10% to about 40% or about 20% to about 30% of *quillaja* saponin by weight.

10. The composition of claim 1, wherein the composition further comprises at least one triglyceride, at least one phospholipid, or a combination thereof.

11. The composition of claim 10, wherein the triglyceride is a medium-chain triglyceride (MCT) or wherein the phospholipid is a lecithin.

12. A method of increasing bioaccessibility and/or bioavailability of an active ingredient in a subject in need thereof, the method comprising administering a therapeutically effective amount of the composition of claim 1 to the subject thereby increasing the bioaccessibility and/or bioavailability of the active ingredient in the subject.

13. The method of claim 12, wherein the bioaccessibility of the active ingredient increases by about 200%.

14. The method of claim 13, wherein the active ingredient is CoQ10, vitamin K-2, vitamin E, resveratrol, or quercetin.

15. A method of preparing a powder comprising the composition of claim 1, the method comprising drying a solution comprising the *quillaja* extract and the at least one active ingredient to form a dried solid and grinding the solid to form a powder comprising the *quillaja* extract and the at least one active ingredient.

16. The method of claim 15, wherein the method comprises:
   a. grinding the at least one active ingredient to form an at least one active ingredient powder;
   b. mixing *quillaja* extract with water to form the *quillaja* extract solution;
   c. mixing the at least one active ingredient powder with *quillaja* extract solution to form a mixture comprising the at least one active ingredient powder and the *quillaja* extract;

d. drying the mixture comprising the at least one active ingredient powder and the *quillaja* extract by stirring or by spray drying to form a dried solid comprising the least one active ingredient powder and the *quillaja* extract; and
e. grinding the solid comprising the at least one active ingredient powder and the *quillaja* extract to form the powder comprising *quillaja* extract and the at least one active ingredient.

17. The composition of claim 1, wherein the *quillaja* extract comprises 10% to 40% or 20% to 30% of *quillaja* saponin by weight.

* * * * *